(12) United States Patent
O'Brien et al.

(10) Patent No.: US 6,712,470 B2
(45) Date of Patent: *Mar. 30, 2004

(54) SYSTEM AND METHOD FOR MEASURING VISION

(75) Inventors: James J. O'Brien, Quakertown, PA (US); Edward R. Mourar, Glenmoore, PA (US)

(73) Assignee: Topcon American Corporation, Paramus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/119,786

(22) Filed: Apr. 10, 2002

(65) Prior Publication Data

US 2003/0193648 A1 Oct. 16, 2003

(51) Int. Cl.[7] .................................................. A61B 3/00
(52) U.S. Cl. ...................................................... 351/245
(58) Field of Search ................................ 351/245, 246, 351/237, 239, 244, 205, 200, 208, 214

(56) References Cited

U.S. PATENT DOCUMENTS

| | | | |
|---|---|---|---|
| 4,437,635 A | | 3/1984 | Pham |
| 4,600,175 A | | 7/1986 | Bell et al. |
| 4,684,088 A | | 8/1987 | Heller |
| 4,790,647 A | * | 12/1988 | Mann et al. ................ 351/245 |
| 5,000,563 A | | 3/1991 | Gisel et al. |
| 5,332,181 A | | 7/1994 | Schweizer et al. |
| 5,444,504 A | * | 8/1995 | Kobayashi et al. ......... 351/237 |
| 5,651,718 A | | 7/1997 | Nakamura |
| 6,095,649 A | | 8/2000 | Brooks et al. |
| 6,105,909 A | | 8/2000 | Wirth et al. |

* cited by examiner

Primary Examiner—George Manuel
(74) Attorney, Agent, or Firm—Volpe and Koenig, P.C.

(57) ABSTRACT

A support system for at least one of ophthalmic and optometric instruments. A first instrument supporting member is pivotable between a first storage position and a first use position. A second instrument supporting member is moveable between a second storage position and a second use position. The patient can be sequentially examined, in any order, by the first and second instruments while remaining in a test position.

27 Claims, 8 Drawing Sheets

SYSTEM AND METHOD FOR MEASURING VISION

BACKGROUND

The present invention is directed to vision measuring systems and, more specifically, to a support system and method for measuring the vision of a patient.

Ophthalmic and optometric instruments are used by ophthalmologists, optometrists and other eye care specialists to help determine the condition of a patient's eyes and eyesight and assist the doctor in determining the amount and nature of corrections that need be made. When examining a patient's eyes, it is common for both the doctor and patient to be seated on opposite sides of an instrument support table which may hold various measuring instruments. Typical tables require that the doctor stand up to manipulate measuring instruments during at least some of the testing. Such manipulations can often not be performed by wheelchair bound examination personnel. Depending on the height of patients, instrument tables are often at an uncomfortable height. This requires patients to either stretch upwardly to place their head in a suitable position or to slump their backs to lower their head to the suitable position. Additionally, typical tables require that the patient adjust their body position depending on the particular test being performed. This tends to increase patient anxiety and interferes with accurate testing.

Clearly, what is needed is an instrument support system that is adjustable depending on the height of a patient, that is handicap accessible, that can be adjusted to fit differently sized wheelchairs, that allows a doctor to stay seated during examination if desired, and that allows a patient to be examined by multiple instruments while remaining in a test position.

SUMMARY

One embodiment of the of the present invention is directed to a support system for at least one of ophthalmic and optometric measuring instruments adapted to measure vision parameters of a patient in a test position defining a patient space. The support system includes a support assembly. A first instrument supporting member is pivotably mounted on the support assembly about a generally vertical axis. The first instrument supporting member is pivotivable between a first storage position and a first use position. The first instrument supporting member is adapted to support a first instrument in the first use position in a defined measuring position. A second instrument supporting member is moveably mounted on the support assembly for motion in a generally vertical plane. The second instrument supporting member is moveable between a second storage position and a second use position. The second instrument supporting member is adapted to support a second instrument in the second use position in the defined measuring position. The patient can be sequentially examined, in any order, by the first and second instruments while remaining in the test position.

In another aspect, the present invention is directed to a method of examining a patient's eyes. The method includes: positioning the patient in a test position defining a patient space; moving a first instrument from a first storage position to a first use position in alignment with a position of the patient's eyes; moving a second instrument from a second storage position to a second use position in alignment with the same position of the patient's eyes, wherein the patient can be sequentially examined, in any order, by the first and second instruments while remaining in the test position.

In another aspect, the present invention is directed to a method of evaluating a patient's vision. The method includes: positioning an evaluator in a seated location at a patient examination station; moving the first instrument from a first storage position to a first use position in alignment with a patient eye position; moving a second instrument from a second storage position to a second use position in alignment with the same patient eye position, wherein the patient can be sequentially examined, in any order, by the first and second instruments while the evaluator remains in the seated position.

BRIEF DESCRIPTION OF THE SEVERAL VIEWS OF THE DRAWINGS

The foregoing summary, as well as the following detailed description of the preferred embodiment of the present invention, will be better understood when read in conjunction with the appended drawings. For the purpose of illustrating the invention, there is shown in the drawings an embodiment which is presently preferred. It is understood, however, that the invention is in not limited to the precise arrangement and instrumentality shown. In the drawings.

DETAILED DESCRIPTION OF THE PREFERRED EMBODIMENT

Certain terminology is used in the following description for convenience only and is not limiting. The words "right," "left," "top," and "bottom" designate directions in the drawings to which reference is made. The words "inwardly" and "outwardly" refer to directions toward and away from, respectively, the geometric center of the support system and designated parts thereof. The term "defined measuring position," as used in the claims and in the corresponding portions of the specification, means "the position that an ophthalmic or an optometric measuring instrument must be located at to evaluate a patient's eyes at a given position." Thus, it is understood that when two instruments are referred to as being positioned at a single defined measuring position, that each instrument, while possibly differently located from the other, is properly positioned to evaluate a patient having his or her eyes at the same geometric position relative to the support system during examination with both instruments. The terminology includes the words above specifically mentioned, derivatives thereof, and words of similar import. Additionally, the words "a" and "one" are defined as including one or more of the referenced item unless specifically stated otherwise.

Referring to FIGS. 1–8, wherein like numerals indicate like elements throughout, a preferred embodiment of a support system for at least one of ophthalmic and optometric measuring instruments is shown and generally designated 10. Briefly stated, the support system 10 allows a patient's eyes to be examined without requiring that the patient readjust his or her head between tests. Additionally, the support system 10 allows an evaluator to examine a patient's eyes while remaining in a seated position at the patient examination station 20. This allows wheelchair bound personnel to comprehensively evaluate a patient's vision parameters while the patient to remains in a single relaxed position (and does not need to readjust his or her head) throughout the testing.

Figure 1:
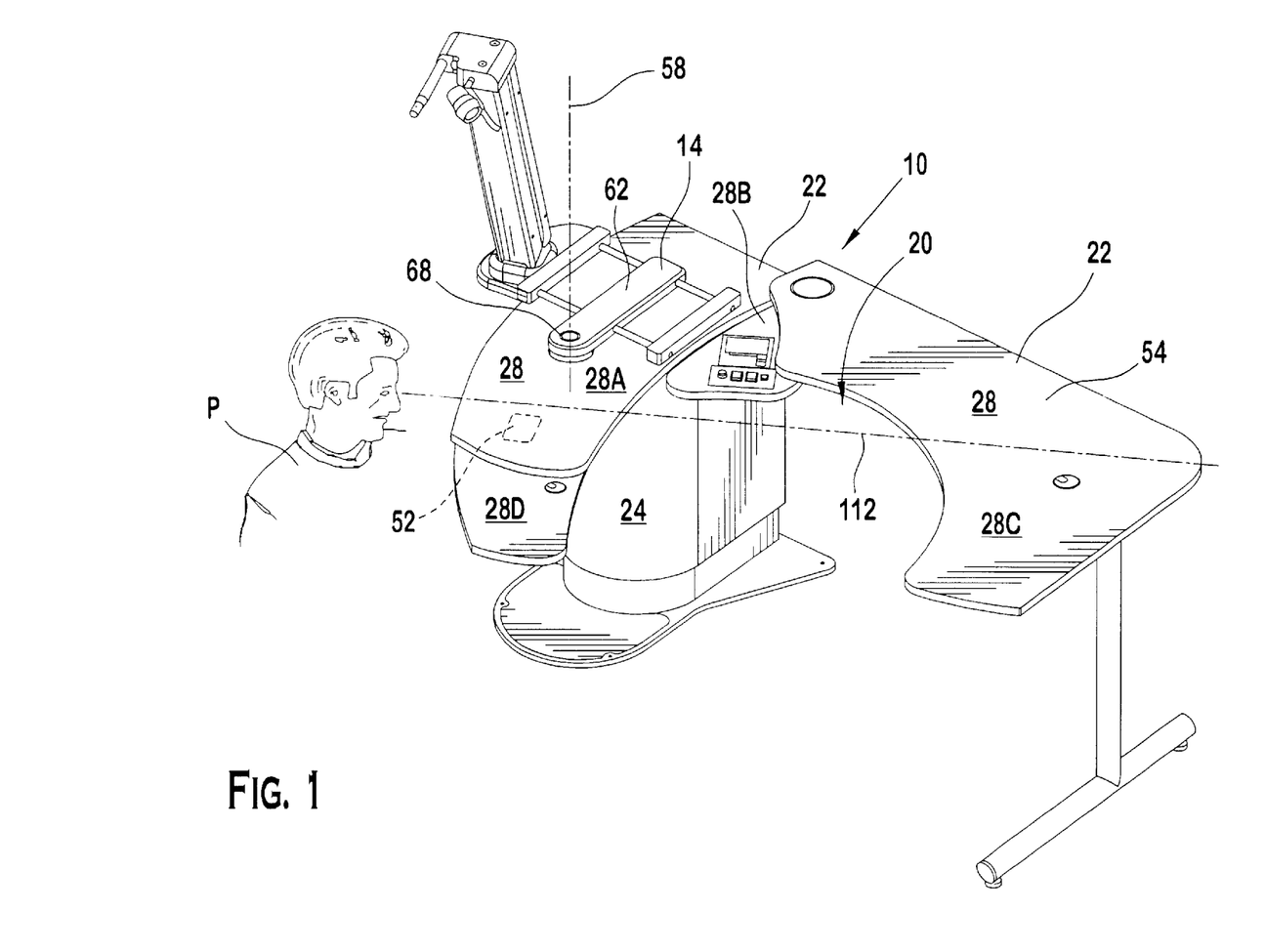
FIG. 1 is a perspective view of a preferred embodiment of a support system according to the present invention.
Figure 2:
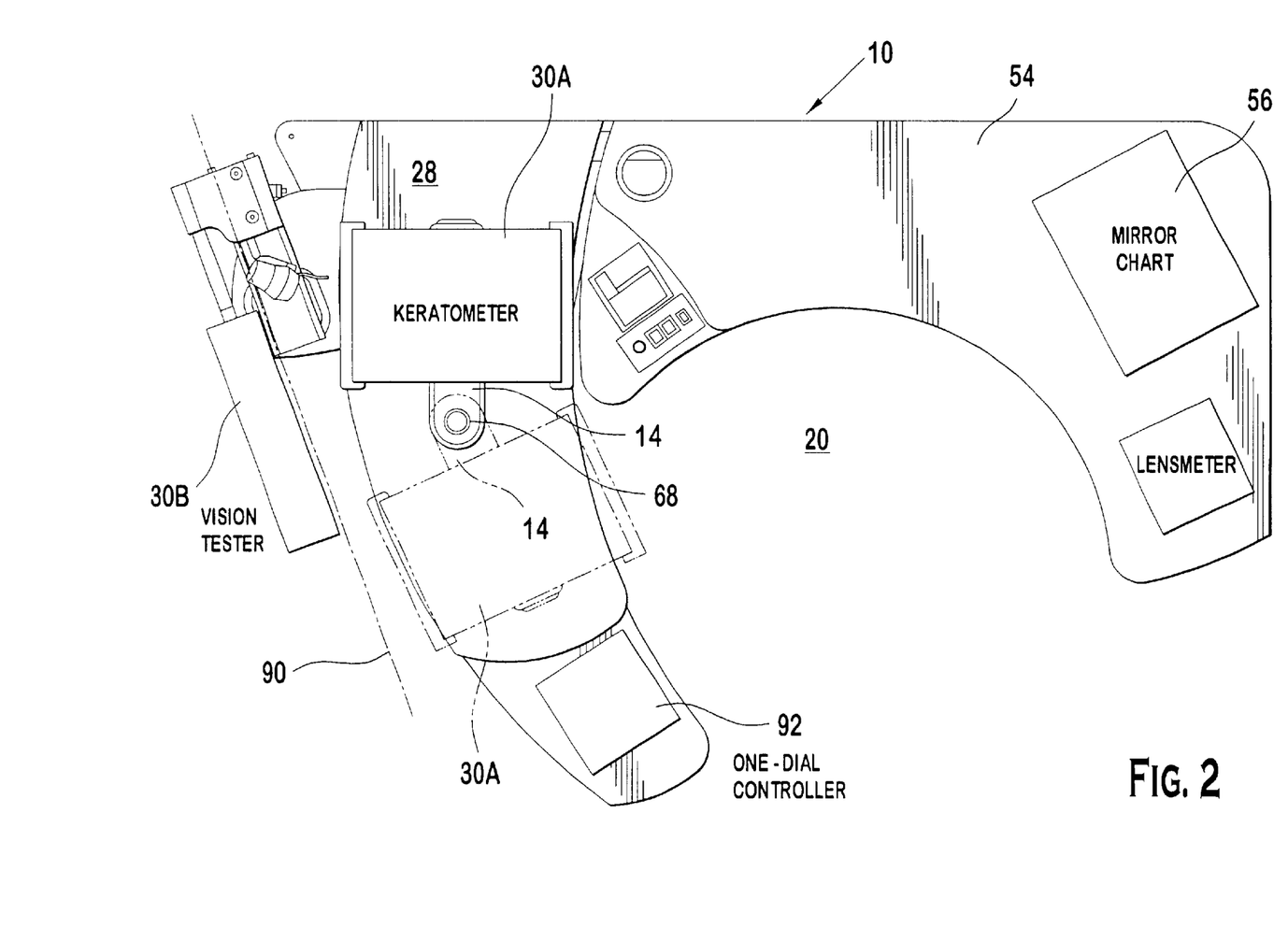
FIG. 2 is a top plan view of the support system of FIG. 1 illustrating a vision tester, a keratometer, a chart, a lensmeter and a one-dial controller positioned on the support system.

Referring to FIGS. 1 and 2, the support system 10 for at least one of ophthalmic and optometric measuring instruments is adapted to measure vision parameters of the patient in a test position defining a patient space. The support system 10 includes a support assembly 22. It is preferred that the housing 24 and its related components are formed from a durable, high strength, low wear material, such as metal. However, those of ordinary skill in the art will appreciate from this disclosure that stainless steel, suitable polymers, alloys and the like can be used without departing from the scope of the present invention. It is preferred that the support system 10 be powered by an electrical motor 26. It is preferred that the electrical motor use power conditioned at 120 volts and 10 amps or at 220 volts at 5 amps. However, those of ordinarily skill in the art will appreciate from this disclosure that hydraulics, battered powered engines, or any other known means of powering the support system 10 can be used without departing from the scope of the present invention.

It is preferred that the table top surfaces 28 of the support system extend generally along an arc of approximately two hundred seventy (270) degrees. This configuration allows a variety of vision measuring devices to be placed on the table surfaces 28 while allowing the support system 10 to remain wheel chair accessible. Additionally, the configuration of the support system 10 allows non handicapped evaluators to comfortably sit at the patient examination station 20 while measuring a patient's vision. The shape of the table surfaces 28 can be varied without departing from the scope of the present invention.

Figure 3:
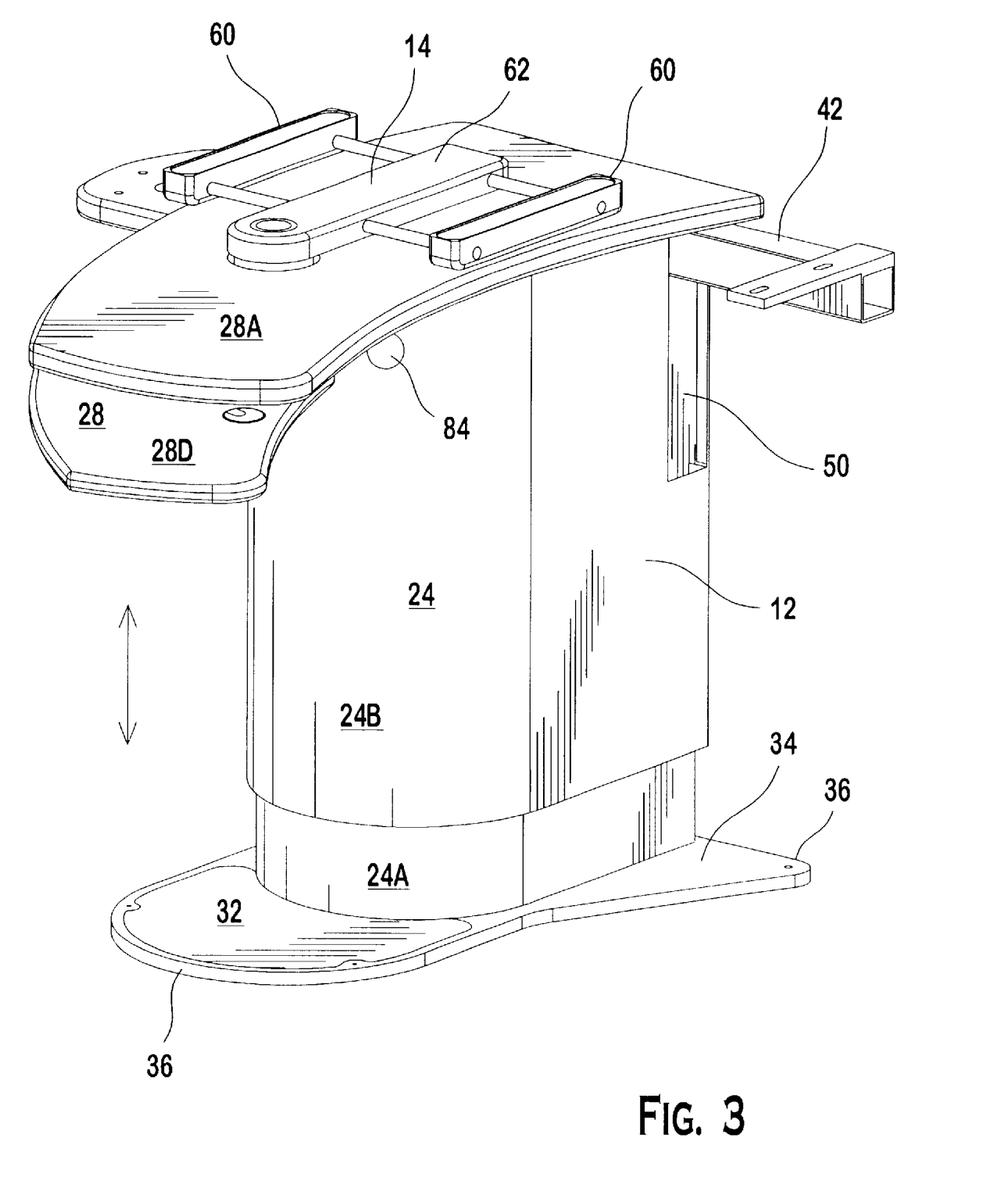
FIG. 3 is a perspective view of a portion of the support system of FIG. 1 that is vertically moveable.
Figure 4:
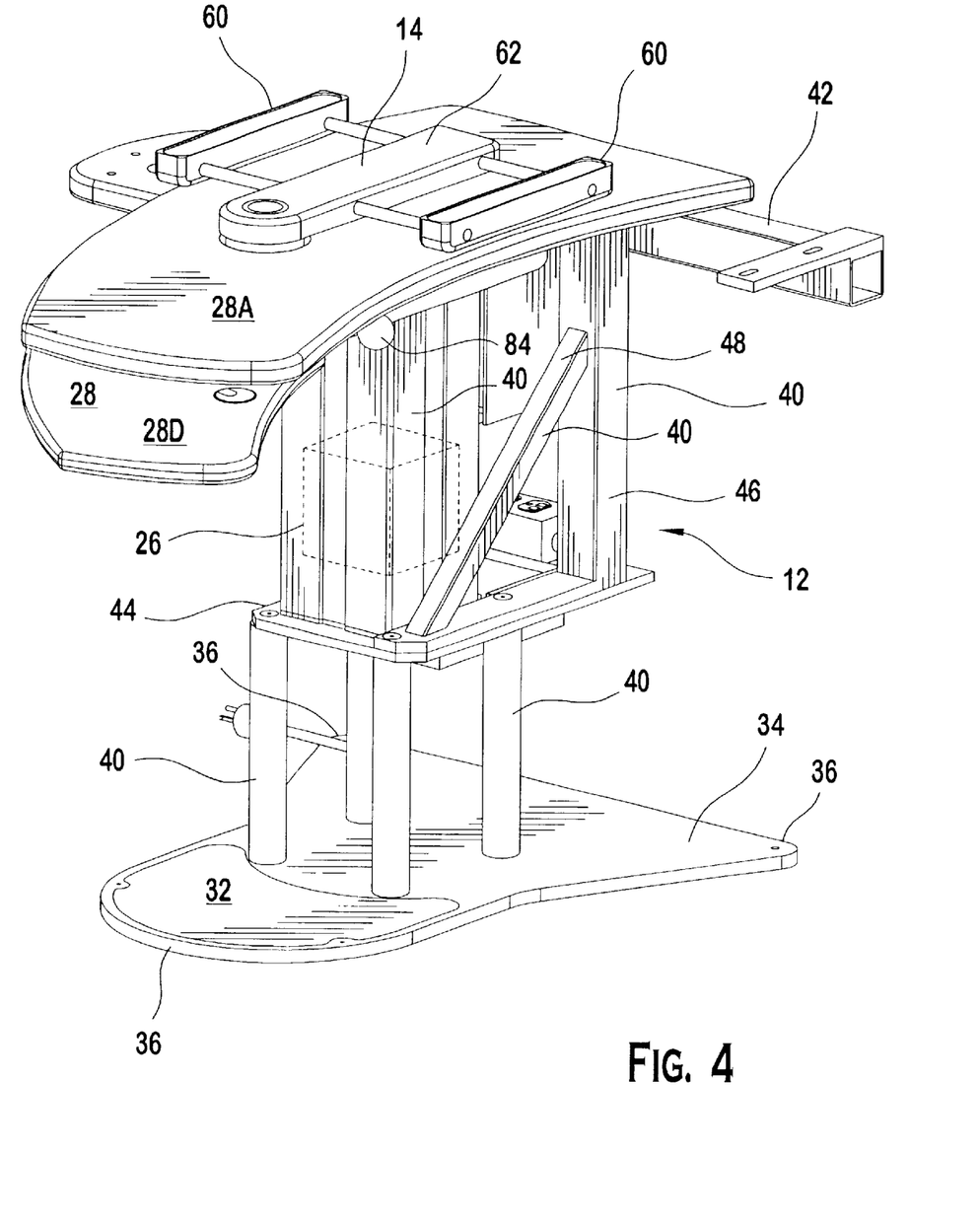
FIG. 4 is a perspective view of a the portion the support system of FIG. 3 with a housing removed.

As best shown in FIGS. 3 and 4, at least a portion 12 of the support assembly 10 that supports first and second instrument supporting members 14, 18 (further described below) is preferably vertically moveable to allow the first and second instruments 30A, 30B (further described below) to be positioned at any one of a plurality of defined measuring positions depending upon the height of the patient. It is preferred that the first portion 12 of the support assembly 22 is vertically adjustable through a range of between two (2) inches and eighteen (18) inches. It is more preferable still that the first portion 12 of the support assembly 22 is vertically adjustable within a vertical range of between about six (6) inches and about eight (8) inches. However, those of ordinary skill in the art will appreciate from this disclosure that the first portion 12 of the support system 10 can be designed to be vertically adjustable for any desired distance. This vertical adjustability allows the instruments 30A, 30B supported by the support system 10 to be positionable and infinitely adjustable along a vertical axis. A footpad 32 is preferably positioned along the bottom left side of the first portion 12 of the support system 10 for stabilization of the support system 10 and to increase the comfort of the patients. The footpad 32 is preferably positioned on a base 34 having three extended ends 36 that provide stability to the support assembly 22.

As best shown in FIG. 4, a tubular frame 40 encloses the motor 26 and supports a connecting arm 42 which extends from the top right portion of the main table surface 28A. The tubular frame 40 preferably has four (4) cylindrical members which extends generally perpendicularly upwardly from the base 34 and are joined at their upper ends by a rectangular frame 44. An L-shaped member 46 is positioned on top of the rectangular frame 44 with a support arm 48 connecting between the two legs of the L shaped member 46. The connecting arm 42 is preferably supported at a fixed height relative to the base 34. Those of ordinary skill in the art will appreciate from this disclosure that any suitable structure can be used to support the first portion 12 of the support 10 without departing from the scope of the present invention.

As best shown in FIG. 3, the housing 24 is formed by an inner housing 24A and an outer housing 24B. The outer housing 24B is configured for slidable movement over the inner housing 24A. The outer housing 24B preferably includes a slot 50 which allows for the main table surface 28A to be raised generally upwardly while the connecting arm 42 (which partially supports the intermediate table surface 28B and the secondary table surface 28C shown in FIG. 1) to be maintained at a constant height relative to the base 34.

Referring to FIG. 1, the support system 10 preferably includes a sensor 52 positioned on the portion 12 of the support assembly 22 which supports the first and second instrument supporting members 14, 18. The sensor 52 is preferably adapted to detect when the first portion 12 of the support assembly 22 contacts and/or approaches a patient's space. The support sensor 52 is preferably positioned proximate to a bottom surface of one or both of the main table surface 28A and the adjustable table surface 28D. Thus, when a patient elects to sit at the support system 10 during evaluation, the table surfaces 28 will not impact a patient's knees or upper leg. As an additional safety feature, it is preferred that the first portion 12 of the support assembly 22 has a nominal speed of approximately one half (½) of an inch per second. However, those of ordinary skill in the art will appreciate that the speed of vertical adjustment of the first portion 12 of the support system 10 can be varied without departing from the scope of the present invention. It is preferred that the sensor 52 is a contact or proximity sensor.

Referring to FIGS. 1 and 2, it is preferred that support assembly 22 include a second portion 54 that is adapted to support a chart 56 to measure the patient's vision (possibly in combination with one or both of the first and second instruments 30A, 30B) The chart 56 is preferably positioned in alignment position with the defined measuring position for testing a patient in the test position. It is preferred, but not necessary, that the second portion of the supportive assembly be positioned at a fixed height. One of ordinary skill in the art will appreciate from this disclosure that the support system 10 can be manufactured such that all the table surfaces 28A–28D are vertically adjustable without departing from the scope of the present invention.

Figure 5:
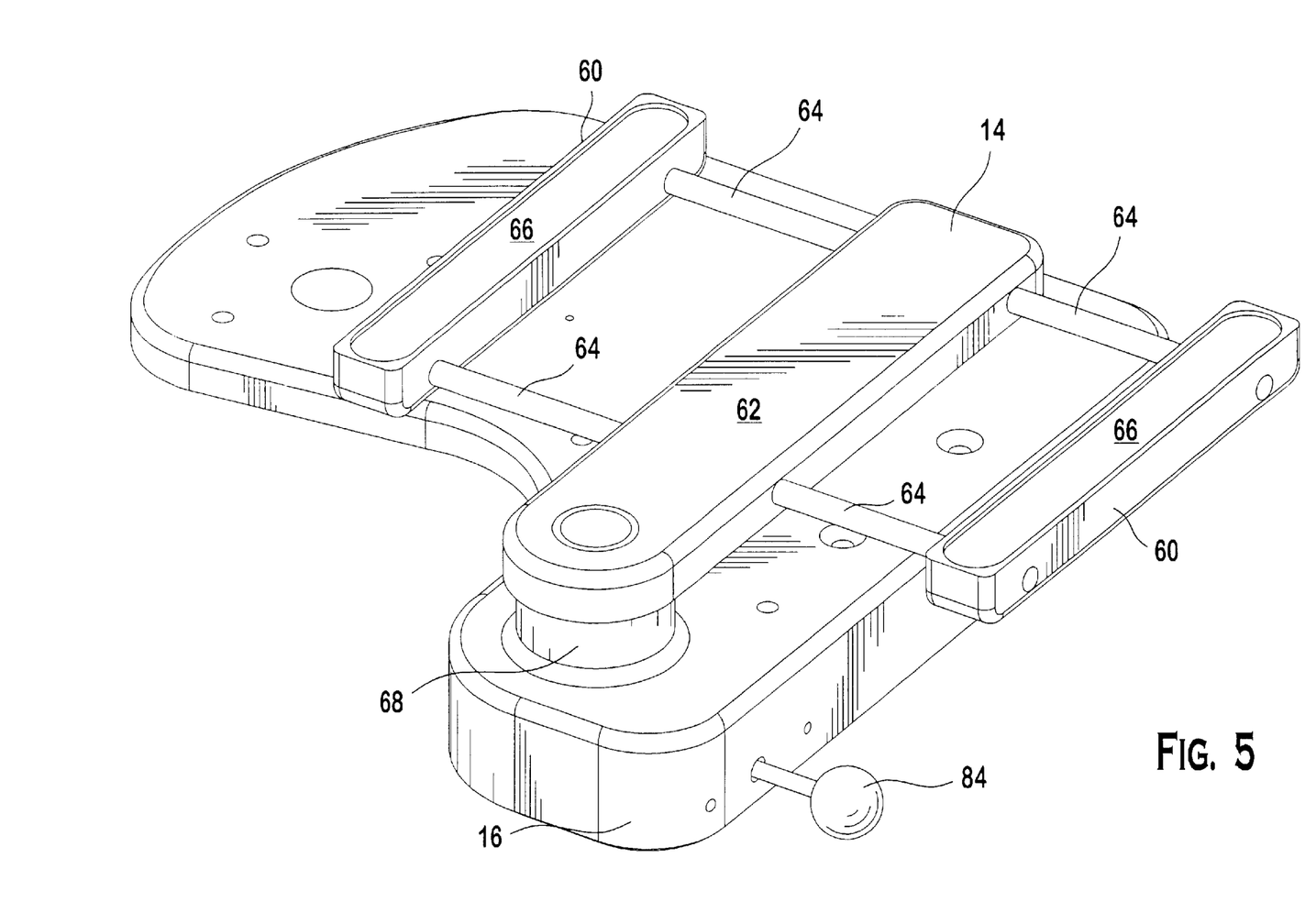
FIG. 5 is a perspective view of a first instrument supporting member interconnected with a mounting plate.

The first instrument supporting number 14 is pivotally mounted on the support assembly 22 about a generally vertical axis 58. The first instrument supporting member 14 is pivotable between a first storage position (shown in FIG. 2 in solid lines) and a first use position (shown in FIG. 2 in phantom lines). It is preferred that the first instrument supporting member 14 be pivotable through an arc of between about twenty-five (25) degrees and about two hundred sixty (260) degrees. It is more preferable that the first instrument supporting member 14 is pivotable through an arc of between sixty (60) degrees and two hundred (200) degrees when moving between the first storage position and the first use position. However, those of ordinary skill in the art will appreciate from this disclosure that the angular range through which the first instrument supporting member 14 can be pivoted can be varied without departing from the scope of the present invention. As best shown in FIG. 5, it is preferable that the first instrument supporting member 14 include two generally parallel support beams 60 that are adapted to support the first instrument 30A thereon. The two support beams 60 are preferably adjustably spaced apart from each other. Each support beam 60 is preferably attached to a main member 62 via rods 64. Each support beam 60 preferably includes an upper surface having a depression 66 into which legs of the first instrument 30A can be seated. Referring to FIG. 2, the first instrument supporting member 14 is adapted to support a first instrument 30A in the first use position (shown in phantom lines) in a defined measuring position.

As mentioned above, the defined measuring position is the position in which the first instrument 30A must be placed in order for it to correspond with the particular eye position of a patient being examined. It is preferred that the first instrument 30A be a keratometer which is supported by the first instrument supporting member 14. However, those of ordinary skill in the art will appreciate that the first instrument 30A can be a slit lamp or any other instrument without departing from the scope of the present invention. A slit lamp is a binocular microscope that allows light to be reflected behind the cornea to inspect eye fibers and eye muscle. The first instrument supporting member 14 is preferably mounted on a hollow shaft 68. A power conduit preferably extends from the interior of the housing 24 through the hollow shaft 68 and the main member 62 to allow the first instrument 30A to be powered without having a dangling extension cord that could interfere with the evaluation process or present a safety hazzard when the first instrument support member 14 is pivoted from the first storage position to the first use position.

Figure 6:
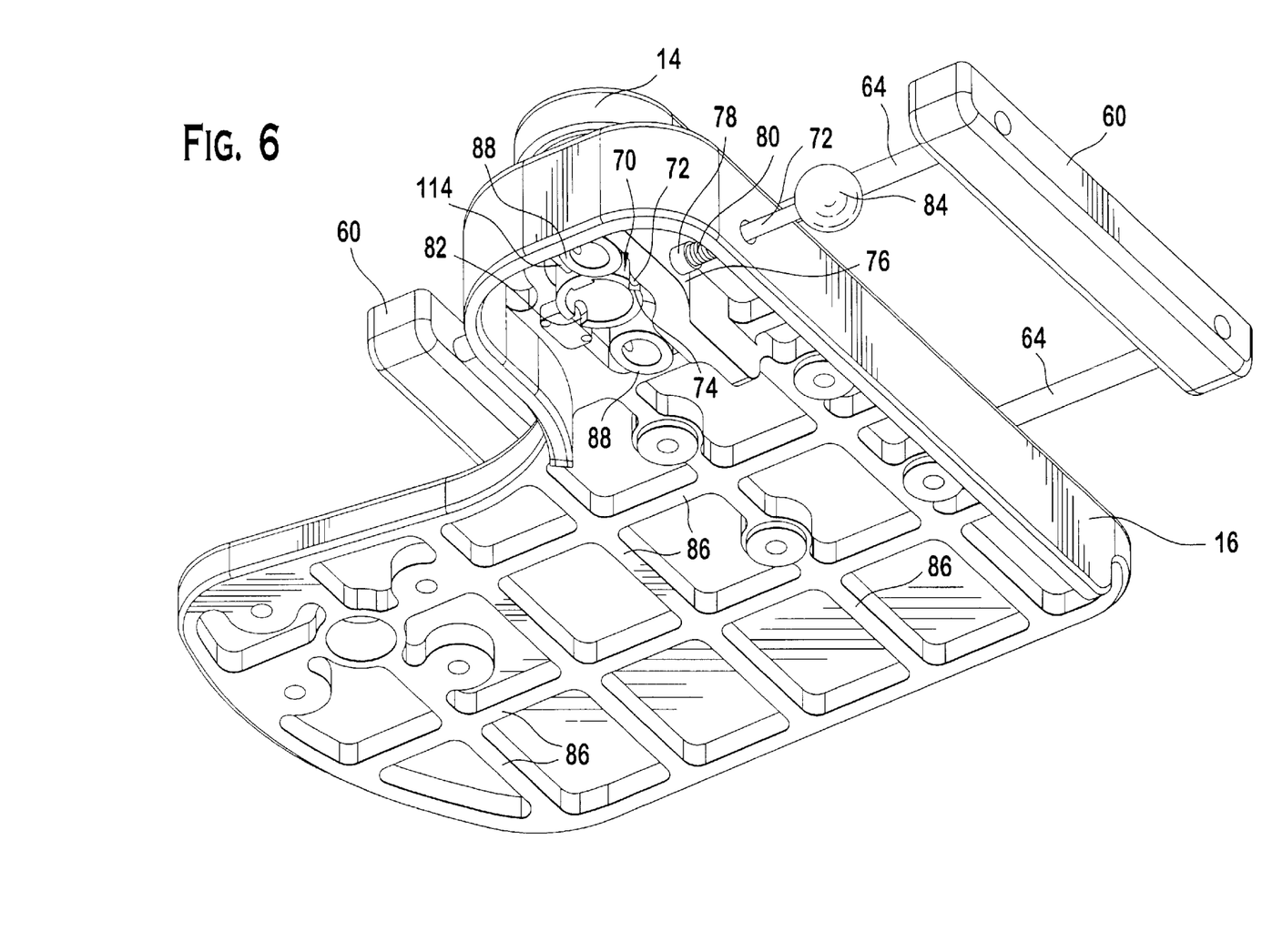
FIG. 6 is a bottom perspective view of the mounting plate of FIG. 5.
Figure 9:
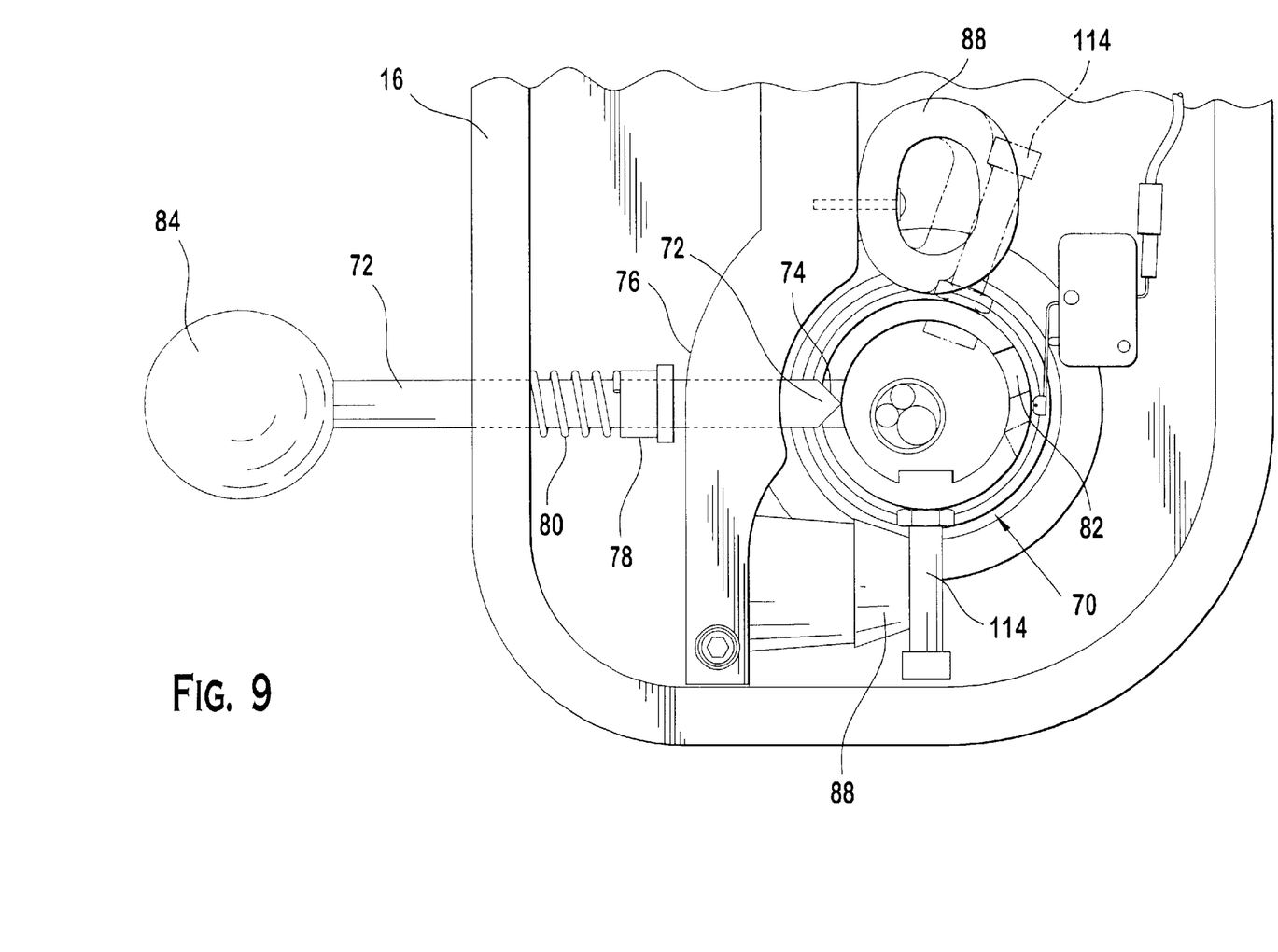
FIG. 9 is an enlarged partial view of the mounting plate of FIG. 6.

Referring to FIGS. 3 and 5, the first instrument support member 14 is preferably interconnected with a mounting plate 16 via the hollow shaft 68 to the mounting plate 16. The mounting plate 16 is preferably positioned underneath the main table surface 28A with the hollow shaft 68 extending through the main table surface 28A such that the first instrument supporting member 14 is pivotably moveable along the main table top surface 28A. It is more preferable that the first instrument supporting member 14 moves above the main table surface 28A so that the first instrument supporting member 14 does not actually touch the main table surface 28A. Referring to FIGS. 6 and 9, it is preferable that a detent mechanism 70 secure the first instrument supporting member 18 in the first storage position. This prevents the first instrument 30A from being accidently moved during patient examination. The detent mechanism 70 is formed by a spring biased rod 72. The rod 72 extends through the mounting plate 16 and is seated within a groove 74 within the hollow shaft 68.

An intermediate wall 76 in combination with the edge of the mounting plate 16, forms a bounded area to limit the inward motion of the spring biased rod 72 due to the placement of a fixed washer or nut 78. A spring 80 is positioned between the edge of mounting plate 16 and the 78 to bias the rods 72 generally inwardly. The shallow depth of groove 74 allows for the inner end of the rod 72 to be displaced when a torque is applied on the hollow shaft 68 by rotating the first instrument supporting member 14. The first instrument supporting member 14 can rotate until a hole 82 is aligned with the inner end of the rod 72 which results in the rod 72 extending further into the hollow shaft 68 and locking the first instrument supporting member 14 in the first use position. To remove the first instrument supporting member 14 from the first use position, an evaluator displaces the handle 84 generally outwardly away from the mounting plate 16 causing the inner end of the rod 72 to be withdrawn from the hollow shaft 68 which results in the first instrument supporting member 14 being pivotable back into the first storage position. It is preferable, that reinforcing ridges 86 are located within the mounting plate 16 to increase the strength of the mounting plate 16. Additionally, it is preferred that the post 114 extend from the hollow shaft 68 at a location above inner end of the rod 72 such that the post 114 contacts polymeric members 88 as the first instrument support 14 approaches either one of the first storage position and the first use position. This slows down the rotation of the first supporting member 14 and acts as shock absorber to provide a smoother stop. It is preferred that the first instrument supporting member 14 is pivotable along a first path, located outside of the patient space, between the first storage position and the first use position.

Figure 7:
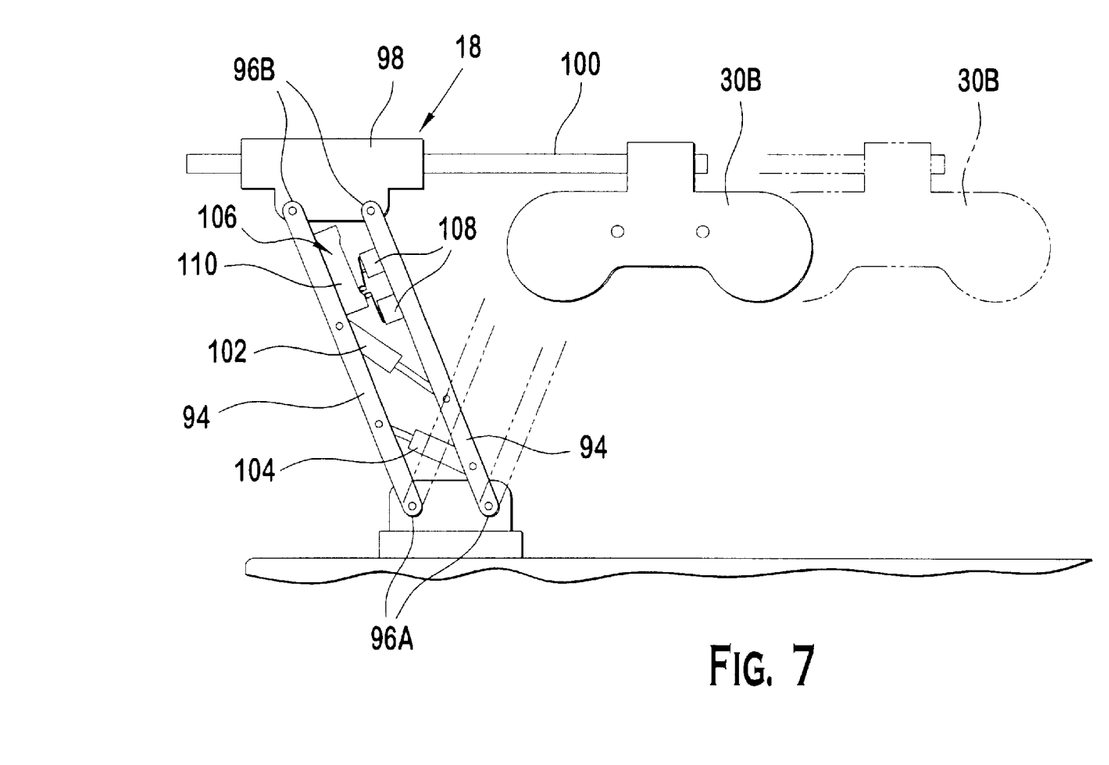
FIG. 7 is a elavational view of a second instrument supporting member.
Figure 8:
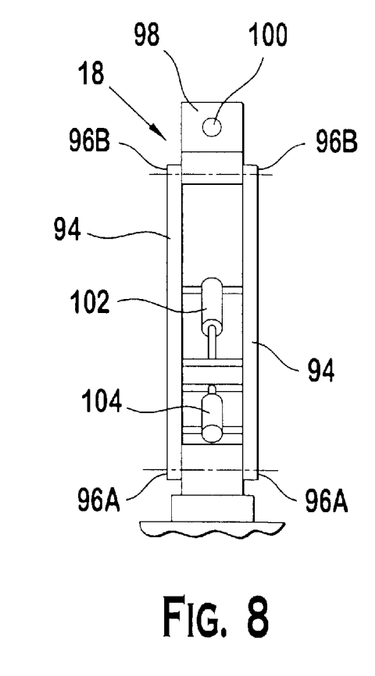
FIG. 8 is a side elavational view of the instrument supporting member of FIG. 7.

Referring to FIGS. 2, 7 and 8, the second instrument supporting number 18 is moveably mounted on the support assembly 22 for motion in a generally vertical plane 90. The second instrument supporting member 18 is moveable between a second storage position (shown in FIG. 7 in solid lines) and a second use position (shown in FIG. 7 in phantom lines). The second instrument supporting member 18 is adapted to support a second instrument 30B in the second use position in the defined measuring position. Accordingly, the second instrument supporting member 18 is configured to move the second instrument 30B to the appropriate location such that the first and second instruments 30A, 30B are each positioned (when in the respective defined measuring position) to evaluate a pair of patient eyes positioned at fixed location depending on the height of the patient. It is preferable that the second instrument 30B is a refractor 30B that is supported by the second instrument supporting member 18. However, those of ordinary skill in the art will appreciate from this disclosure that the second instrument can be any other type of eye related equipment without departing from the scope of the present invention. The refractor 30B can be any one of a manual phoropter or computerized vision tester without departing from the scope of the present invention. It is preferable that the second instrument supporting member 18 is in communication with the controller 92 such that the second instrument supporting member 18 is remotely operable. This allows an evaluator to move the second instrument 30B between the second storage position and the second use position without manually manipulating the instrument 30B. Additionally, the controller preferably includes a safety switch or button that allows the evaluator to arrest the motion of the second instrument supporting member 18 along the path. The evaluator can preferably return the second instrument supporting member 18 to the second storage position by depressing the safety switch or button a second time. This further increases the safety of patients being tested by the evalautor.

As best shown in FIGS. 7 and 8, it preferable that the second instrument supporting member 18 is formed by at least two parallel bars 94 each having a first end 96A mounted for pivoting movement relative to the support assembly 22 and each having a second end 96B pivotably attached to an instrument supporting member 98. Thus, the parallel bars 94, the instrument supporting member 98, and the base form a four bar linkage. It is preferable that two sets of parallel bars are used to increase the stability and strength of the second instrument supporting member 18. An instrument hanger 100 preferably extends laterally from the instrument supporting member 98 to support the second instrument 30B An actuator 102 preferably connects at least two of the parallel bars 94 and is adapted to move the parellel bars 94 between first and second positions to move the second instrument supporting member 18 between the second storage position and the second use position. It is preferable, that the actuator 102 is be a mechanical actuator. However, those of ordinary skill in the art would appreciate that any known actuator device can be used without departing from the scope of the present invention.

The second instrument supporting 18 preferably includes one motion dampening device 104 connected between two parallel bars 94. It is preferable that the motion dampening device 104 include opposingly mounted dash pots to provide smooth movement of the second instrument supporting arm 18 between the second storage position and the second use position.

It is preferred that the second instrument supporting member 18 includes at least one sensor 106 adapted to determine when the second instrument supporting member 18 is approaching any one of the second storage position and the second use position. It is preferred that at least one sensor 106 consist of two micro-switches 108. The micro-switches 108 are preferably mounted on one of the parallel bars 94 (or within the housing enclosing the operating structure of the second instrument supporting member 18) in facing opposition to a ramp 110. As the second instrument support member 18 approaches either one of the second storage position and the second use position, a micro-switch follower is depressed by a portion of the ramp extending generally rightwardly which sends a signal to the controller 92 to begin deceleration of the second instrument supporting member 18.

The second instrument supporting member 18 is preferably a pivotable through a second path, located outside the patient space, between the second storage position and the second use position. The controller 92 preferably prevents the second instrument supporting member 18 from leaving the second storage position until the first instrument supporting member 14 is located in the first storage position. This safety feature prevents damage to the first and second instruments 30A, 30B and, more importantly, prevents injury to a patient due to evaluator inattention.

The support system 10 of the present invention allows the patient to be sequentially examined, in any order, by the first and second instruments 30A, 30B while remaining in the test position. The term "remaining in the test position," as used in the claims and in the corresponding portions of the specification, is defined to mean "while not having to move the patient's head during testing." However, depending upon a patient's sensitivity, it is expected that minor head movements may occur due to the approach of the first instrument or second instrument 30A, 30B without departing from the scope of the present invention. The present invention significantly improves the testing of patient's vision parameters by not requiring patients to realign their head with separate instruments during successive tests. Additionally, the support system 10 allows a seated evaluator to examine the patient's vision with multiple instruments without having to stand up in order to manipulate various opthalmalic and optometric measuring instruments.

A first preferred method of examining a patient's eyes according to the present invention includes positioning the patient in a test position defining a patient space. Moving the first instrument 30A from the first storage position to the first use position in alignment with the position of the patient's eyes. Moving the second instrument 30B from the second storage position to the second use position in alignment with the position of the patient's eyes, wherein the patient can be sequentially examined, in any order, by the first and second instruments 30A, 30B while remaining in the test position.

The method preferably includes the step of locating a chart 56 adapted to measure the patient's vision such that the chart is properly positioned for testing while the patient is in the test position. The chart 56 is preferably used with the refractor 30B.

A second preferred method of evaluating a patient's vision according to the present invention includes positioning the evaluator in a seated location at the patient examination station. Moving the first instrument 30A from the first storage position to the first use position in alignment with a patient eye position. Moving the second instrument 30B from the second storage position to the second use position in alignment with the same patient eye position, wherein the patient can be sequentially examined, in any order, by the first and second instruments 30A, 30B while the evaluator remains in the seated position. Either the first or second preferred method of the present invention preferably includes the movement of the second instrument 30B between the second storage position and the second use position being remotely controlled by the evaluator.

Referring to FIGS. 1–8, the preferred embodiment of the present of the invention operates as follows, a patient positions themselves along the left side of the support assembly 22 as shown in FIG. 1 so that the patient's line of sight extends generally along axis 112 depending upon the patient's preference and height, the patient can be sitting or standing. Then, an evaluator preferably rotates the first instrument supporting member 14 from the first storage position into the first use position. Then, the evaluator can measure the patient's vision with the first instrument 30A. Afterwards, the evaluator displaces the handle 84 to allow the first instrument supporting member 14 to be pivoted from the first use position back into the first storage position. Once the first instrument 30A is in the first storage position, the evaluator can use the controller 92 to move the second instrument supporting member 18 from the second storage position into the second use position. When the first and second instruments 30A, 30B are in their respective use positions, they are each aligned to measure a patient's eyes which are positioned throughout the examinations at the same location. Thus, the patient does not have to move his or her head during the examination. Additionally, due to the vertical adjustability of the instruments, the patient is able to sit in a natural and relaxed manner throughout the testing. This facilitates greater accuracy of test results. While the patient is using the refractor 30B, a chart can be positioned generally along the viewing axis 112, if desired.

Once the patient's vision has been measured using the second instrument 30B, the evaluator uses the controller 92 to move the second instrument supporting member 18 from the second storage position back into the first storage position.

The support system 10 of the present invention allows a patient's vision to be evaluated without the patient and/or the evaluator having to adjust their positions during the testing. It is recognized by those skilled in the art, that changes may be made to the above described embodiments of the invention without departing from the broad inventive concept thereof. It is understood, therefore, that this invention is not limited to the particular embodiments disclosed, but is intended to cover all modifications which are within the spirit and scope of the invention as defined by the appended claims.

We claim:

1. A support system for at least one of ophthalmic and optometric measuring instruments adapted to measure vision parameters of a patient in a test position defining a patient space, the support system comprising:
    a support assembly forming at least part of a table top;
    a first instrument supporting member which provides a generally planar instrument support surface and is pivotably mounted on the support assembly about a generally vertical axis, the first instrument supporting member being pivotable between a first storage position and a first use position, wherein the first instrument supporting member is adapted to support a first instrument in the first use position in a defined measuring position; and
    a second instrument supporting member moveably mounted on the support assembly for pivotal motion in a generally vertical plane about at least one point proximate to the table top, the second instrument supporting member being movable between a second storage position and a second use position, wherein the second instrument supporting member is adapted to support a second instrument in the second use position in the defined measuring position, wherein the patient can be sequentially examined, in any order, by the first and second instruments while remaining in the test position.

2. The support system of claim 1, wherein the first instrument supporting member is pivotable through a first path, located outside the patient space, between the first storage position and the first use position, the second instrument supporting member is pivotable through a second path, located outside of the patient space, between the second storage position and the second use position.

3. The support system of claim 1, wherein the first instrument is a keratometer that is supported by the first instrument supporting member and the second instrument is a refractor that is supported by the second instrument supporting member.

4. The support system of claim 3, wherein the second instrument supporting member is in communication with a controller such that the second instrument supporting member is remotely operable.

5. The support system of claim 1, wherein at least a portion of the support assembly supporting the first and second instrument supporting members is vertically moveable to allow the first and second instruments to be positioned to any one of a plurality of defined measuring positions depending upon a height of the patient.

6. The support system of claim 5, wherein the support assembly includes a second portion that is adapted to support a chart to measure the patient's vision, the chart being positioned in an aligned position with the defined measuring position for testing while the patient is in the test position.

7. The support system of claim 6, wherein the second portion of the support assembly is at a fixed height.

8. The support system of claim 5, further comprising a sensor positioned on the portion of the support assembly supporting the first and second instrument supporting members, the sensor being adapted to detect when the portion of the support assembly contacts and/or approaches the patient space.

9. The support system of claim 5, wherein the sensor is a contact sensor.

10. The support system of claim 1, wherein the first instrument supporting member is pivotable between sixty (60) degrees and two hundred (200) degrees when moving between the first storage position and the first use position.

11. The support system of claim 10, wherein the first instrument supporting member comprises two generally parallel support beams adapted to support the first instrument thereon, the two generally parallel support beams being adjustably spaced apart from each other.

12. The support system of claim 1, further comprising a detent mechanism for securing the first instrument supporting member in the first use position.

13. The support system of claim 1, further comprising a controller that prevents the second instrument supporting member from leaving the second storage position until the first instrument supporting member is located in the first storage position.

14. A support system for at least one of ophthalmic and optometric measuring instruments adapted to measure vision parameters of a patient in a test position defining a patient space, the support system comprising:
    a support assembly;
    a first instrument supporting member pivotably mounted on the support assembly about a generally vertical axis, the first instrument supporting member being pivotable between a first storage position and a first use position, wherein the first instrument supporting member is adapted to support a first instrument in the first use position in a defined measuring position;
    a second instrument supporting member moveably on the support assembly for motion in a generally vertical plane, the second instrument supporting member being movable between a second storage position and a second use position, wherein the second instrument supporting member is adapted to support a second instrument in the second use position in the defined measuring position, wherein the patient can be sequentially examined, in any order, by the first and second instruments while remaining in the test position;
    at least two parallel bars each having a first end mounted for pivoting movement relative to the support assembly and each having a second end pivotally attached to an instrument supporting member; and
    an actuator connecting the at least two parallel bars and adapted to move the at least two parallel bars between first and second positions to move the second instrument supporting member between the second storage position and the second use position.

15. The support system of claim 14, wherein the second instrument supporting member comprises at least one motion dampening device connected between the at least two parallel bars.

16. The support system of claim 14, wherein the second instrument supporting member further comprises at least one sensor adapted to determine when the second instrument supporting member is approaching any one of the second storage position and the second use position.

17. The support system of claim 16, wherein the at least one sensor comprises two micro switches.

18. A method of examining a patient's eyes, comprising:

positioning the patient in a test position defining a patient space positioned proximate to a table top;

moving a first instrument from a first storage position to a first use position in alignment with a position of the patient's eyes, the first instrument being supported by a first instrument supporting member that provides a generally planar support surface and pivots along the table top about a vertical axis;

moving a second instrument from a second storage position to a second use position in alignment with the same position of the patient's eyes, the second instrument being supported by a second instrument supporting member that has at least one pivot point located proximate to the table top, wherein the patient can be sequentially examined, in any order, by the first and second instruments while remaining in the test position.

19. The method of claim 18, wherein the first instrument is moved through a first path, outside of the patient space, between the first storage position and the first use position, the second instrument is moved through a second path, outside of the patient space, between the second storage position and the second use position.

20. The method of claim 18, further comprising the step of:

locating a chart adapted to measure the patient's vision such that the chart is properly positioned for testing while the patient is in the test position.

21. A method of evaluating a patient's vision, comprising:

positioning an evaluator in a seated location at a patient examination station including a table top;

moving a first instrument from a first storage position to a first use position in alignment with a patient eye position, the first instrument being guided during movement by a first instrument supporting member that provides a generally planar support surface and pivots along the table top about a vertical axis;

moving a second instrument from a second storage position to a second use position in alignment with the same patient eye position, the second instrument being guided during movement by a second instrument supporting member that has at least one pivot point located proximate to the table top, wherein the patient can be sequentially examined, in any order, by the first and second instruments while the evaluator remains in the seated position.

22. The method of claim 21, wherein the first instrument is moved through a first path, outside of the patient space, between the first storage position and the first use position, the second instrument is moved through a second path, outside of the patient space, between the second storage position and the second use position.

23. The method of claim 22, wherein the movement of the second instrument between the second storage position and the second use position is remotely controlled by the evaluator.

24. The method of claim 23, further comprising the step of the evaluator operating a controller to arrest the motion of the second instrument along the second path.

25. The method of claim 24, further comprising the step of the evaluator operating the controller a second time to return the second instrument to the second storage position.

26. The method of claim 24, wherein the operating of the controller comprises the evaluator depressing a button and/or switch.

27. The method of claim 21, further comprising the step of:

locating a chart adapted to measure the patient's vision such that the chart is aligned with the patient eye position for tenting while the patient is in the test position.

* * * * *

UNITED STATES PATENT AND TRADEMARK OFFICE
CERTIFICATE OF CORRECTION

PATENT NO.    : 6,712,470 B2
DATED         : March 30, 2004
INVENTOR(S)   : O'Brien et al.

It is certified that error appears in the above-identified patent and that said Letters Patent is hereby corrected as shown below:

Column 3,
Line 34, after the word "hydraulics", delete "battered" and insert therefor -- battery --.

Column 6,
Line 67, after the word "the", delete "evalautor" and insert therefor -- evaluator --.

Column 7,
Line 24, after the word "supporting", insert -- arm --.

Column 10,
Line 40, after the word "moveably", insert -- mounted --.

Column 12,
Line 35, after the word "for", delete "tenting" and insert therefor -- testing --.

Signed and Sealed this

Twenty-fourth Day of August, 2004

JON W. DUDAS
*Director of the United States Patent and Trademark Office*